United States Patent

Takaki et al.

[11] Patent Number: 5,850,835
[45] Date of Patent: Dec. 22, 1998

[54] RESPIRATOR SYSTEM

[75] Inventors: Toshihisa Takaki; Mikio Yasukawa, both of Shizuoka; Hiroshi Takabayashi, Tokyo; Yasuhito Sugiura, Shizuoka; Katuyoshi Suzuki, Shizuoka; Masahiro Kamada, Shizuoka; Yoshitugu Yamada, 1-37-14, Daizawa, Setagaya-ku, Tokyo; Kazufuku Nitta, Saitama, all of Japan

[73] Assignees: Suzuki Motor Corporation, Shizuoka; Metran Medical Instrument Mfg. Co. Ltd., Tokyo; Japan Science and Technology Corporation, Saitama; Yoshitugu Yamada, Tokyo, all of Japan

[21] Appl. No.: 835,035

[22] Filed: Mar. 27, 1997

[30] Foreign Application Priority Data

Mar. 28, 1996 [JP] Japan ................................. 8-099428

[51] Int. Cl.$^6$ ............................................. A61M 16/00
[52] U.S. Cl. ................................ 128/204.18; 128/204.21; 128/205.24
[58] Field of Search ..................... 128/204.18, 204.21, 128/204.23, 204.24, 204.25, 205.24, 205.19

[56] References Cited

U.S. PATENT DOCUMENTS

| | | | |
|---|---|---|---|
| 2,918,917 | 12/1959 | Emerson | 128/205.19 |
| 4,172,467 | 10/1979 | Warnow | 137/494 |
| 4,543,951 | 10/1985 | Phuc | 128/205.19 |
| 4,630,605 | 12/1986 | Pasternack | 128/205.24 |

*Primary Examiner*—Aaron J. Lewis
*Attorney, Agent, or Firm*—Greenblum & Bernstein P.L.C.

[57] ABSTRACT

A respirator system is composed of a blower unit for supplying and vacuuming air, a control valve for selecting a positive pressure and a negative pressure from the blower unit to send a vibrating air pressure, a diaphragm for vibrating in connection to the vibrating air pressure to send respiration gas to a patient, and a hollow housing partitioned by the diaphragm into a first pressure chamber cooperating with the vibrating air pressure and a second pressure chamber cooperating with the respiration gas.

In addition, the respirator system is further composed of a sensor for sensing the position of the diaphragm in the hollow housing, a pressure regulator for increasing or decreasing the positive pressure and the negative pressure, and a pressure controller for driving and controlling the pressure regulator based on data on the diaphragm position outputted from the sensor.

In the respirator system, the pressure regulator increases or decreases the positive pressure and the negative pressure. Thereby, responsiveness can be remarkably improved.

5 Claims, 4 Drawing Sheets

RESPIRATOR SYSTEM

BACKGROUND OF THE INVENTION

1. Field of the Invention

The present invention relates to a respirator system for supplying air forcedly to a patient having difficulty in spontaneous respiration and for reducing patient load once spontaneous respiration has occurred.

2. Description of the Prior Art

FIG. 4 shows a block diagram of a conventional respirator system. Referring to FIG. 4, the conventional respirator system will be described below.

A conventional respirator 50 is composed of a blower unit 52 where air pressures of both a positive pressure Ap and a negative pressure An are concurrently produced, a control valve 54 for converting the positive pressure Ap or the negative pressure An into a predetermined vibrating air pressure Apn by alternately selecting the positive pressure Ap and the negative pressure An produced in the blower unit 52, a hollow housing 56 having a diaphragm 561 for providing air to a patient P in which the vibrating air pressure Apn from the control valve 54 operates, a diaphragm neutral position controller 60 for maintaining a neutral position of the diaphragm 561 in the hollow housing 56, and a respiration gas supply portion 62 for supplying respiration gas.

The blower unit 52 has a positive pressure line 521 and a negative pressure line 522, and aspirates air through the negative pressure line 522 and discharges the air through the positive pressure line 521. An orifice line 523 open to outside air is connected to the negative pressure line 522.

The control valve 54 has a rotary valve mechanism and includes a rotary valve 544 with ports 541, 542, 543 and a driving portion 545 for rotating the rotary valve 544. The driving portion 545 is composed of a motor and a reduction gear (both are not shown) and rotates the rotary valve 544, for example, at 900 rpm (revolutions per minute). The rotary valve 544 opens only the port 541 and the port 543 once per revolution and subsequently opens only the port 542 and the port 543 once. A vibrating air pressure line 546 for transmitting the vibrating air pressure Apn to the hollow housing 56 is connected to the port 543. A flow rate control valve 547 is connected to the vibrating air pressure line 546.

The hollow housing 56 includes a first pressure chamber 562, a second pressure chamber 563 and a diaphragm 561 formed of a retractable member for partitioning the first pressure chamber 562 and the second pressure chamber 563. The first pressure chamber 562 is connected to the vibrating air pressure line 546.

The respiration gas supply portion 62 is composed of a blender 621 for aspirating and mixing outside air and preliminary prepared oxygen and a humidifier 622 for humidifying the air discharged from the blender 621. A respiration line 623 for providing respiration Ai to the patient P via the humidifier 622 is connected to the humidifier 622. A pressure chamber 563 is connected to the respiration line 623 and a pressure sensor 624 is connected near the patient P.

The respirator system 60 is composed of a diaphragm position sensor 601 for detecting the position of the diaphragm 561, a control line 603 for connecting the positive pressure line 521 and the vibrating air pressure line 546 via the orifice 602, a control line 604 for connecting the respiration line 623 and the vibrating air pressure line 546, a flow rate control valve 605 for communicating the control line 603 with outside air, and a pressure controller 606 for controlling the flow rate control valve 605 based on the diaphragm 561 position detected with the diaphragm position sensor 601. The pressure controller 606 has a function of controlling a flow rate control valve 607 for communicating the control line 604 with outside air based on a pressure in the respiration line 623 detected by the pressure sensor 624.

Operation of the respirator 50 and the respirator system 60 will be described.

The vibrating air pressure Apn produced by the rotary valve 54 is transmitted to the hollow housing 56. In the hollow housing 56, the diaphragm 561 is vibrated by a cycle of the vibrating air pressure Apn. The vibration of the diaphragm 561 changes the pressure in the respiration line 623. The respiration Ai is constantly provided to the patient P. Expiration of the patient P is discharged from the flow rate control valve 607. The flow rate control valve 607 is normally open so as to discharge the expiration.

The concave-convex operation of the diaphragm 561 is detected by the diaphragm position sensor 601 and is outputted constantly to the pressure controller 606 as operation data of the diaphragm 561. If the concavo-convex operation of the diaphragm 561 is disturbed due to the spontaneous respiration, the data is immediately outputted to the pressure controller 606. Then, the pressure controller 606 controls the flow rate control valves 605, 607 to control the pressure in the respiration line 623. Thereby, burden of the patient P in conducting spontaneous respiration is reduced.

If the neutral position of the diaphragm 561 is off-center, reciprocating motion of the diaphragm 561 is limited, thereby the respiration operation of the respirator 50 becomes insufficient. Therefore, the control line 604 acts to keep the neutral position of the diaphragm 561 in the center by reducing a differential pressure between the pressure chamber 562 and the pressure chamber 563 small so as not to disturb the operation of the hollow housing 56. In a case where the action of the control line 604 is insufficient, the pressure controller 606 acts as follows:

The pressure controller 606 constantly determines misalignment of the neutral position of the diaphragm 561 based on the operation data of the diaphragm 561. When the neutral position of the diaphragm 561 is shifted to the patient P side, the pressure controller 606 opens the flow rate control valve 605 to decrease the vibrating air pressure Apn. On the other hand, when the neutral position of the diaphragm 561 is shifted to the blower unit 52, the pressure controller 606 closes the flow rate control valve 605 to increase the vibrating air pressure Apn.

However, the conventional respirator system 60 has the following problems.

First, responsiveness in controlling the neutral position of the diaphragm 561 is inferior. This problem results in low detecting accuracy because spontaneous respiration is detected from the diaphragm 561 position.

Second, it is insanitary because air in the blower unit 52 side may be contaminated with air in the patient P side through the control line 604.

SUMMARY OF THE INVENTION

An object of the present invention is to provide a respirator system capable of improving the responsiveness in controlling the neutral position of the diaphragm and preventing the air at the blower unit side from contaminating the air at the patient side.

Through intense studies of the present inventors for achieving the object, the following discoveries were obtained.

In the prior art, controlling the neutral position of the diaphragm 561, in other words, controlling the vibrating air pressure Apn is simply equal to adjusting the degree of openness of the positive pressure Ap component of the vibrating air pressure Apn to atmosphere. Therefore, not only the positive pressure Ap component but also the negative pressure An component are controlled, thereby improving the responsiveness. In addition, the vibrating air pressure Apn is open not to atmosphere but to the negative pressure An side or the positive pressure Ap side, thereby the differential pressure is greater. Consequently, the responsiveness can be improved. As a result, the control line 604 is omitted.

According to the present invention, a respirator system is composed of a blower unit for supplying and vacuuming air, a control valve for selecting a positive pressure and a negative pressure from the blower unit to send a vibrating air pressure, a diaphragm for vibrating in connection to the vibrating air pressure to send respiration gas to a patient, and a hollow housing partitioned by the diaphragm to a first pressure chamber cooperating with the vibrating air pressure and a second pressure chamber cooperating with the respiration gas.

According to the present invention, the respirator system is further composed of a sensor for sensing a position of the diaphragm in the hollow housing, a pressure regulator for increasing or decreasing the positive pressure and the negative pressure, and a pressure controller for driving and controlling the pressure regulator based on data on the diaphragm position outputted from the sensor.

In the respirator system of the present invention, the pressure regulator increases or decreases the positive pressure and the negative pressure of the blower unit to control the vibrating air pressure. Thereby, responsiveness can be remarkably improved.

In other words, according to one embodiment of the present invention, a positive pressure releasing line and a negative pressure releasing line are disposed, thereby improving the responsiveness. According to another embodiment, a negative pressure application line and a positive pressure application line are disposed to be capable of opening the vibrating air pressure not to atmosphere but to the positive pressure side or the negative pressure side, thereby a greater differential pressure can be utilized. Consequently, the responsiveness can be further improved.

With improvement in the responsiveness, the diaphragm is immediately maintained at a neutral position. Thereby, detectability of the diaphragm position can be improved. Accordingly, detectability of spontaneous respiration can also be improved.

In addition, the control line for communicating the air at the blower unit side and the air at the patient side which is conventionally required for controlling the neutral position of the diaphragm can be omitted. Consequently, the air at the blower unit side and the air at the patient side can be fully separated, resulting in being sanitary.

DETAILED DESCRIPTION OF THE PREFERRED EMBODIMENTS

Figure 1:
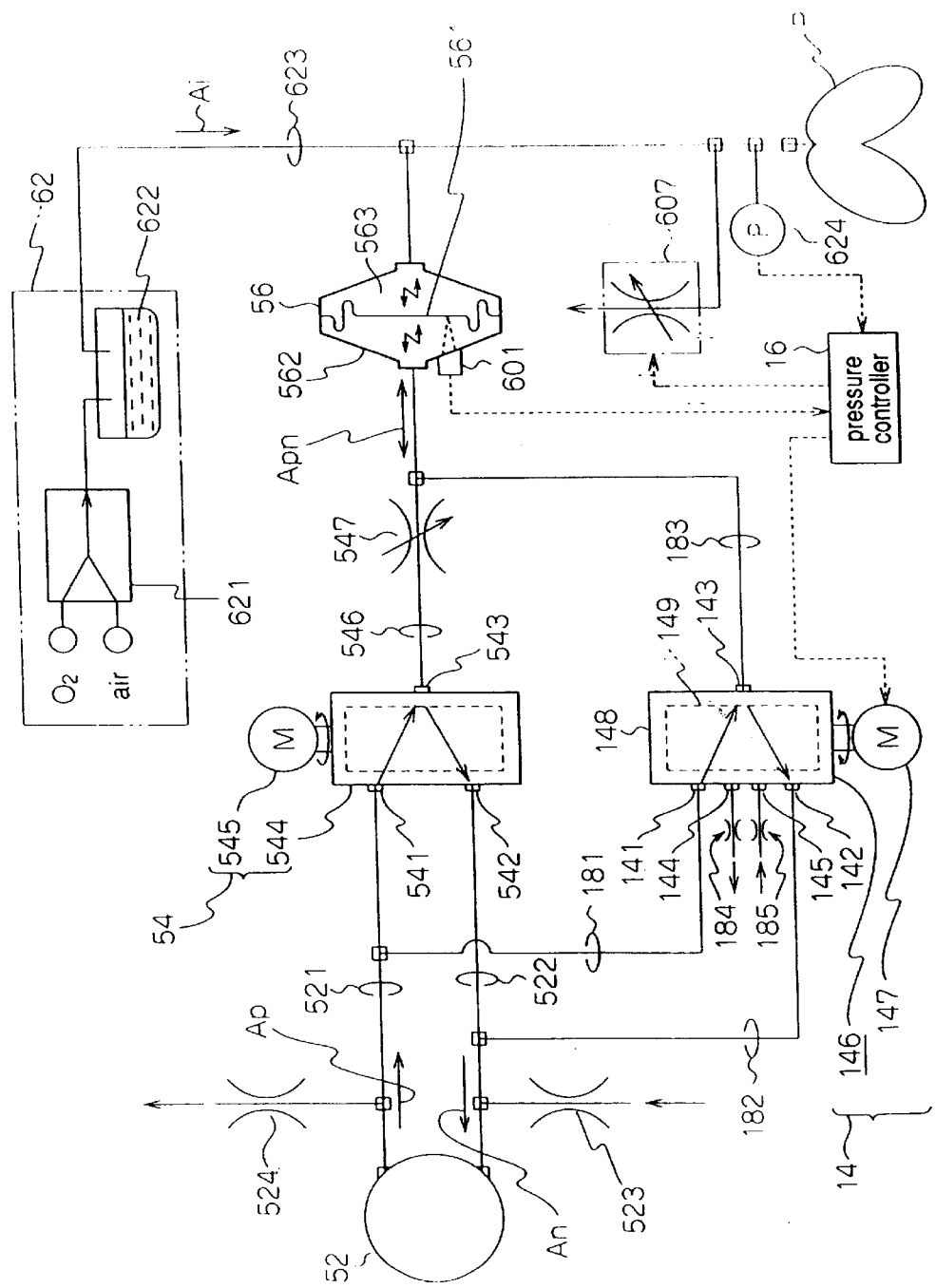
FIG. 1 is a block diagram showing one embodiment of a respirator system according to the present invention.
Figure 4:
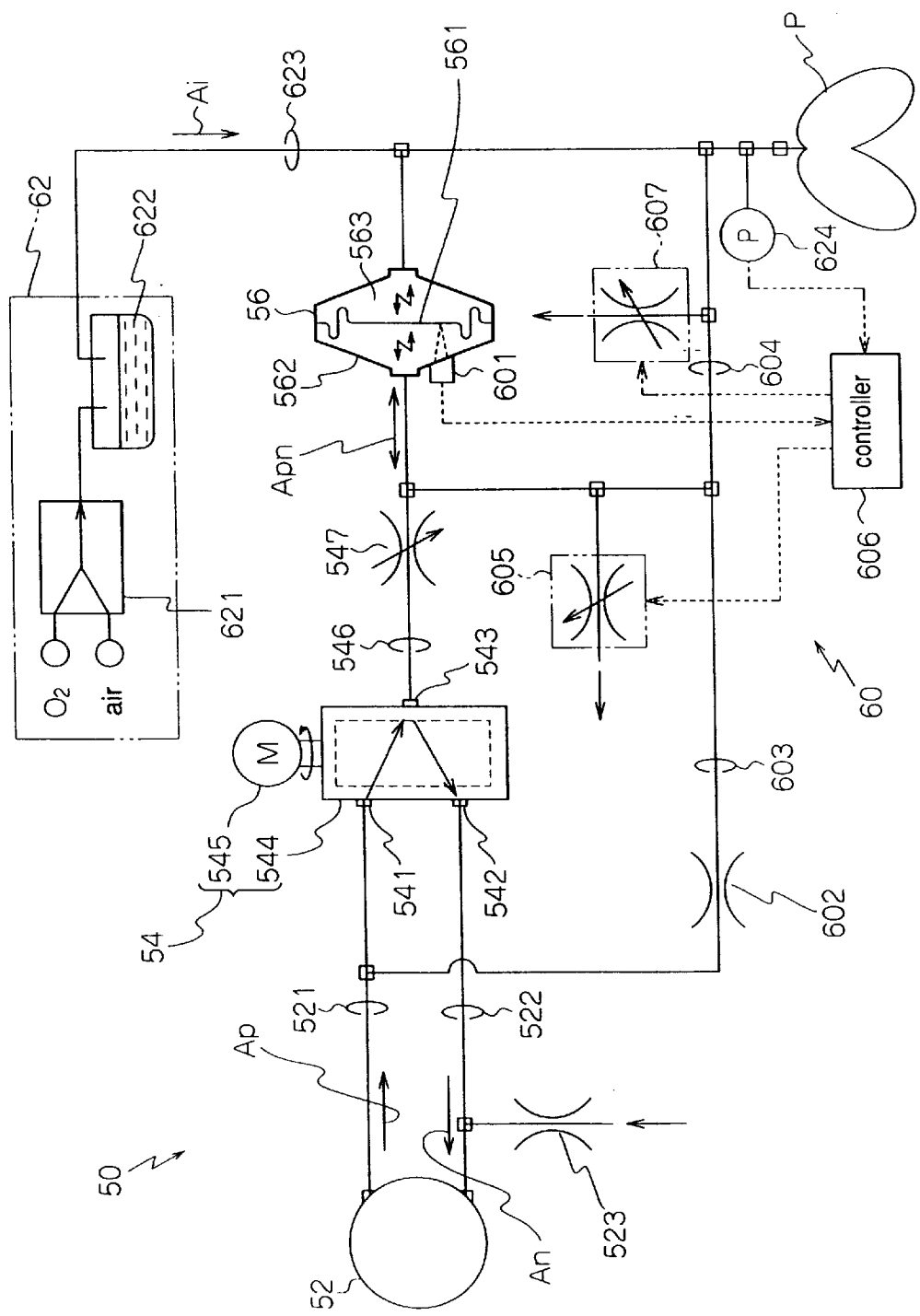
FIG. 4 is a block diagram showing a conventional respirator and a respirator system.

FIG. 1 is a block diagram showing one embodiment of a respirator and a respirator system according to the present invention. Referring to FIG. 1, the embodiment will be described. Same portions are provided with the same symbols as in FIG. 4 and their descriptions are not repeated.

The respirator system 10 of the present embodiment is composed of a blower unit 52 for producing both air pressures of a positive pressure Ap and a negative pressure An, a control valve 54 for converting the positive pressure Ap and the negative pressure An into a predetermined vibrating air pressure Apn by alternately selecting the positive pressure Ap and the negative pressure An produced in the blower unit 52, a hollow housing 56 having a diaphragm for providing air to a patient P in which the vibrating air pressure Apn from the control valve 54 operates, a diaphragm position sensor 601 for detecting the position of the diaphragm 561 in the hollow housing 56, a pressure regulator 14 for controlling the positive pressure Ap, the negative pressure An or the vibrating air pressure Apn and a pressure controller 16 for controlling the pressure regulator 14 based on the position of the diaphragm 561 detected with the diaphragm position sensor 601.

The pressure regulator 14 is structurally similar to the rotary valve and is composed of a main body 146 having ports 141 to 145, and an actuator 147 for reciprocally rotating a part of the main body 146. The actuator 147 is composed of a motor and a reduction gear (both are not shown) and rotates the part of the main body 146 at a desired angle. The pressure controller 16 is a microcomputer composed, for example, of a CPU, ROM, RAM, an I/O interface or the like. An orifice line 524 being open to outside air is connected to the positive pressure line 521.

Figure 2:
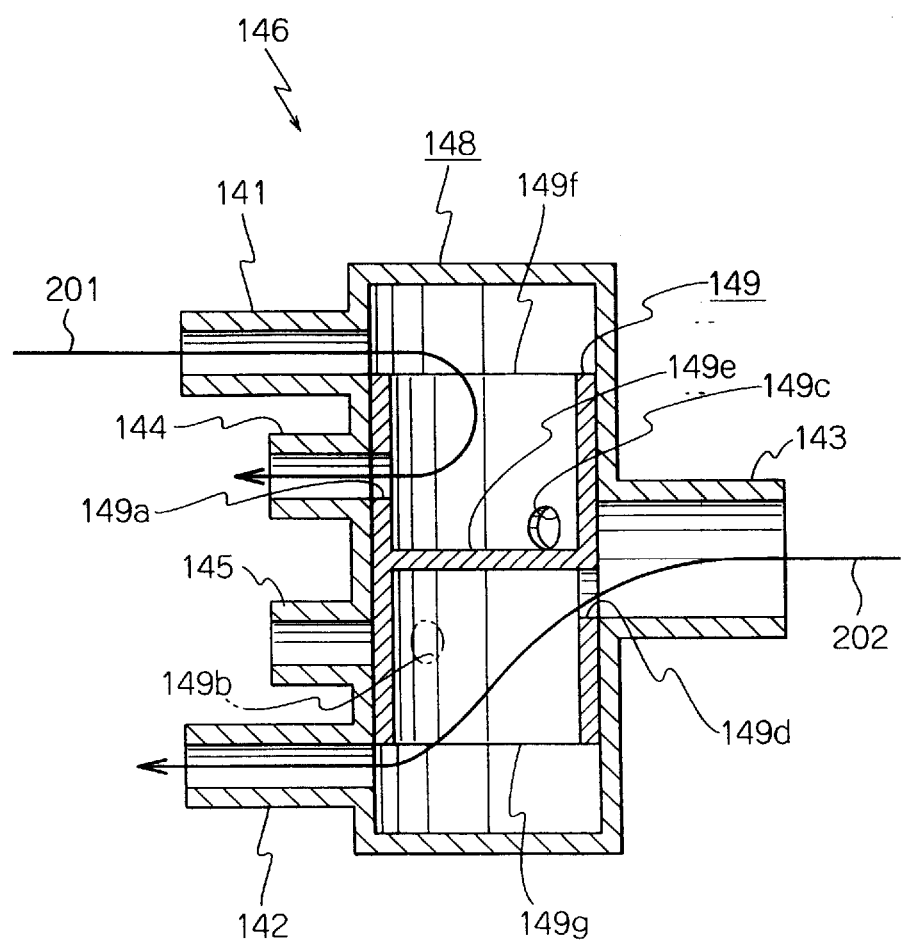
FIG. 2 is a sectional view showing one embodiment of a pressure control valve main body in the respirator system in FIG. 1, where a positive pressure releasing line and a negative pressure applying line are selected.
Figure 3:
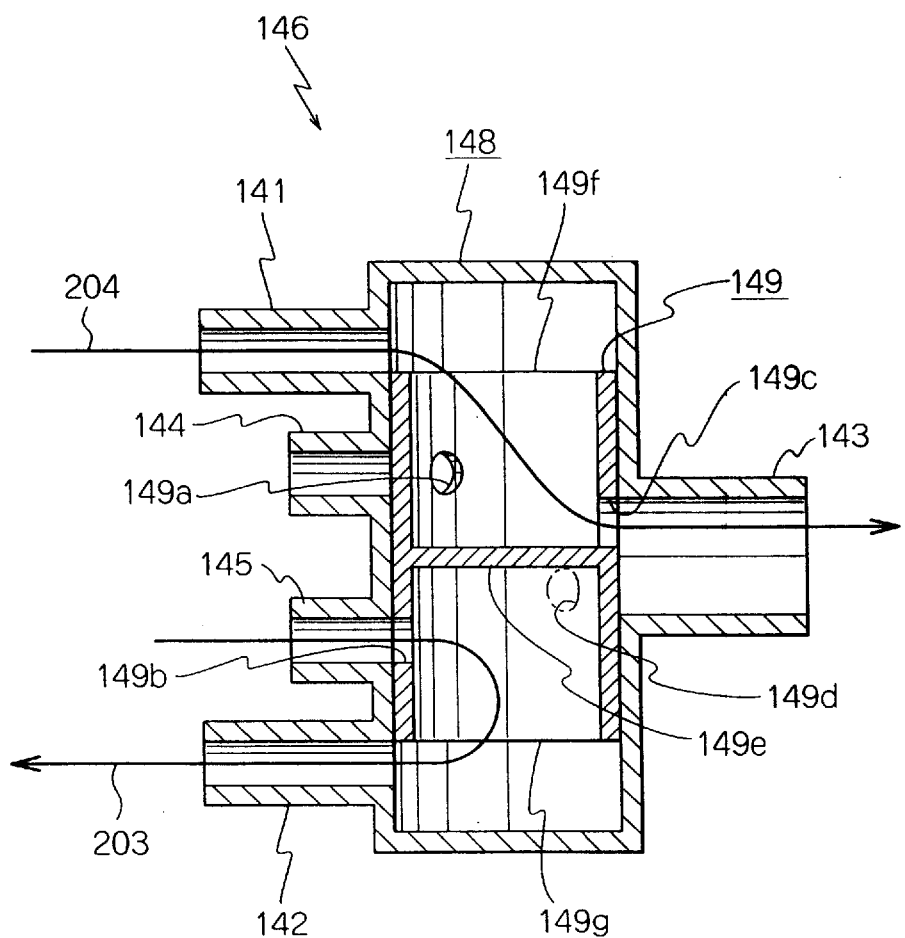
FIG. 3 is a sectional view showing one embodiment of a pressure control valve main body in the respirator system in FIG. 1, where a negative pressure releasing line and a positive pressure applying line are selected.

FIGS. 2 and 3 are sectional views showing embodiments of the main body 146 of the pressure regulator 14. Referring to FIGS. 1 to 3, the embodiment will be described.

The main body 146 is composed of a stator 148 in an outer tube and a rotor 149 in an inner tube inscribed to the stator 148. The ports 141 to 145 are disposed at the stator 148. Clearances 149a, 149b, 149c, 149d, a partition 149e and open ends 149f, 149g are disposed at the rotor 149.

A positive bypass line 181 communicating with the positive pressure line 521 is connected to the port 141. A negative bypass line 182 communicating with the negative pressure line 522 is connected to the port 142. A vibrating air pressure bypass line 183 communicating with the vibrating air pressure line 546 is connected to the port 143. Atmosphere open ports 184, 185 are connected to the ports 144, 145, respectively.

The rotor 149 is rotated by the actuator 147. The rotor 149 can select either one of the positive pressure releasing line 201 and the negative pressure applying line 202 (FIG. 2) or the negative pressure releasing line 203 and the positive pressure applying line 204 (FIG. 3) corresponding to its rotating angle.

The positive pressure releasing line 201 is an air proceeding line through the positive pressure bypass line 181, the port 141, the open end 149f, the clearance 149a, the port 144, the orifice line 184, and decreases the absolute value of the positive pressure Ap produced in the blower unit 52.

The negative pressure applying line 202 is an air proceeding line through the vibrating air pressure bypass line 183, the port 143, the clearance 149d, the open end 149g, the port 142, the negative pressure bypass line 182, and applies the negative pressure An produced in the blower unit 52 to the vibrating air pressure Apn for urging the diaphragm 561.

The negative pressure releasing line 203 is an air proceeding line through the orifice line 185, the port 145, the open end 149g, the port 142, the negative pressure bypass line 182, and decreases an absolute value of the negative pressure An produced in the blower unit 52.

The positive pressure applying line 204 is an air proceeding line through the positive pressure bypass line 181, the port 141, the open end 149f, the clearance 149c, the port 143, the vibrating air pressure bypass line 183, and applies the positive pressure Ap produced in the blower unit 52 to the vibrating air pressure Apn for urging the diaphragm 561.

The amount of air flowing through each line can be continuously changed by rotating the rotor 149 at small angular intervals with the actuator 147. At a specific angle of the rotor 149, it is possible not to select any lines.

Operation of the respirator system 10 will be described.

The pressure controller 16 constantly determines misalignment of the average neutral position of the diaphragm 561 based on operation data of the diaphragm 561 obtained through the diaphragm position sensor 601. When the average neutral position of the diaphragm 561 is misaligned, the pressure controller operates as follows:

When the neutral position of the diaphragm 561 is shifted to the patient P side (right side in FIG. 1), the pressure controller selects the positive pressure releasing line 201 and the negative pressure applying line 202 of pressure regulator 14. Then, the absolute value of the positive pressure Ap produced in the blower unit 52 is decreased by the positive pressure releasing line 201 and the negative pressure An produced in the blower unit 52 is applied to the vibrating air pressure Apn by the negative pressure applying line 202, thereby decreasing the vibrating air pressure Apn. Consequently, the neutral position of the diaphragm 561 returns to the center (left side in FIG. 1).

On the other hand, when the neutral position of the diaphragm 561 is shifted to the blower unit 52 side (left side in FIG. 1), the pressure controller selects the negative pressure releasing line 203 and the positive pressure applying line 204. Then, the absolute value of the negative pressure An produced in the blower unit 52 is decreased by the negative pressure releasing line 203 and the positive pressure Ap produced in the blower unit 52 is applied to the vibrating air pressure Apn by the positive pressure applying line 204, thereby increasing the vibrating air pressure Apn. Consequently, the neutral position of the diaphragm 561 returns to the center.

Time required to return the diaphragm 561 to the neutral position can be shorter than that for conventional ones because not only the positive pressure Ap but also the negative pressure An are controlled. In addition, the vibrating air pressure Apn is open not to atmosphere, but to the negative pressure An side or the positive pressure Ap side. Thereby, a large differential pressure can be utilized to further shorten the time.

It is obvious that the present invention is not limited to the above preferred embodiments. For example, the rotor 149 may select either of the positive pressure releasing line 201 or the negative pressure releasing line 203, or either of the negative pressure applying line 202 or the positive pressure applying line 204.

The entire disclosure of Japanese Patent Application No. 8-99428 filed on Mar. 28, 1996 including the specification, claims, drawings and summary are incorporated herein by reference in its entirety.

What is claimed is:

1. A respirator system comprising:

a blower unit for supplying and vacuuming air, a control valve for selecting a positive pressure and a negative pressure from the blower unit to send a vibrating air pressure, a diaphragm for vibrating with the vibrating air pressure to send respiration gas to a patient, a hollow housing partitioned by the diaphragm into a first pressure chamber cooperating with the vibrating air pressure and a second pressure chamber cooperating with the respiration gas, a sensor for sensing the position of the diaphragm in the hollow housing, a pressure regulator for increasing or decreasing the positive pressure and the negative pressure; and a pressure controller for driving and controlling the pressure regulator based on data on the diaphragm position outputted from the sensor.

2. The respirator system according to claim 1, wherein the pressure regulator includes:

a positive pressure releasing line for releasing the positive pressure produced in the blower unit to atmosphere, a negative pressure releasing line for releasing the negative pressure produced in the blower unit to atmosphere; and an actuator for switching the negative pressure releasing line and the positive pressure releasing line.

3. The respirator system according to claim 1, wherein the pressure regulator includes means for changing the vibrating air pressure cooperating with either one of the first and second pressure chambers of the hollow housing.

4. The respirator system according to claim 3, wherein the pressure regulator includes:

a positive pressure applying line for applying the positive pressure produced in the blower unit to the vibrating air pressure urging the diaphragm, a negative pressure applying line for applying the negative pressure produced in the blower unit to the vibrating air pressure urging the diaphragm; and an actuator for switching the negative pressure applying line and the positive pressure applying line.

5. The respirator system according to claim 1, wherein the pressure regulator includes:

a positive pressure releasing line for decreasing the absolute value of the positive pressure produced in the blower unit, a negative pressure applying line for applying the negative pressure produced in the blower unit to the vibrating air pressure urging the diaphragm, a negative pressure releasing line for decreasing the absolute value of the negative pressure produced in the blower unit, a positive pressure applying line for applying the positive pressure produced in the blower unit to the vibrating air pressure urging the diaphragm; and an actuator for switching the positive pressure releasing line and the negative pressure applying line or the negative pressure releasing line and the positive pressure applying line.

\* \* \* \* \*